United States Patent [19]

Brodbeck

[11] Patent Number: 5,359,905

[45] Date of Patent: Nov. 1, 1994

[54] FUEL CHECKER FOR USE WITH PET COCK OR BALL AND SPRING DRAIN VALVES

[76] Inventor: Robert M. Brodbeck, 9310 S. Watson Gulch Rd., Littleton, Colo. 80127

[21] Appl. No.: 966,289

[22] Filed: Oct. 26, 1992

[51] Int. Cl.⁵ .................. G01N 1/12; G01N 33/22
[52] U.S. Cl. .................. 73/863.86; 73/61.43; 73/61.61; 73/426; 73/863.85; 73/864.63; 73/864.65
[58] Field of Search ........... 73/863.71, 863.81, 863.85, 73/863.86, 864.51, 864.63, 864.65, 426–429, 61.43, 61.44, 61.55, 64.56, 61.61

[56] References Cited

U.S. PATENT DOCUMENTS

| | | | |
|---|---|---|---|
| 1,571,055 | 1/1926 | Hutchins | 73/863.86 |
| 3,011,349 | 12/1961 | Kratz | 73/863.86 |
| 3,198,016 | 8/1965 | Poorman | 73/863.86 |
| 3,976,572 | 8/1976 | Reick | 73/61.43 |
| 4,289,027 | 9/1981 | Gleaves et al. | 73/863.86 |
| 4,304,132 | 12/1981 | Snaper | 73/61.61 |
| 4,700,580 | 10/1987 | Kamin | 73/864.51 |
| 4,967,595 | 11/1990 | Olson | 73/864.51 |

OTHER PUBLICATIONS

Sporty's Pilot Shop catalog, Oshkosh Issue, Aug. thru Nov. 1992, p. 65.

Primary Examiner—Hezron E. Williams
Assistant Examiner—George M. Dombroske

[57] ABSTRACT

A hand-manipulative apparatus is disclosed for receiving a specimen of the fuel tank contents of a fuel tank. The apparatus comprises an elongated body of substantially circular cross-section. The body is fabricated of transparent molded material and is open at its upper end. The body is of tubular character through a portion of its length for defining a fuel-receiving compartment having a central axis and communicating with the open upper end of the body. The body has spaced-apart indentations in its upper end edge for alignment and cooperation with associated actuating arms of a pet cock drain valve, if such a pet cock drain valve is utilized. The tubular portion is closed at its lower end portion. A resilient semi-rigid rod is removably attached at a first end to the lower end portion of the tubular portion. The resilient rod extends along the central axis beyond the upper end edge of the body so as to engage and manipulate a ball and spring drain valve at a second end of the rod, if such a ball and spring drain valve is utilized. Additionally, the rod is supported at an intermediate portion thereof. Supporting the rod at the first end (lower end) provides much more effective use with ball and spring type drain valves making it much less flimsy and incapable of being pushed down the elongated body during use by the opposing force of the ball and spring valve.

17 Claims, 1 Drawing Sheet

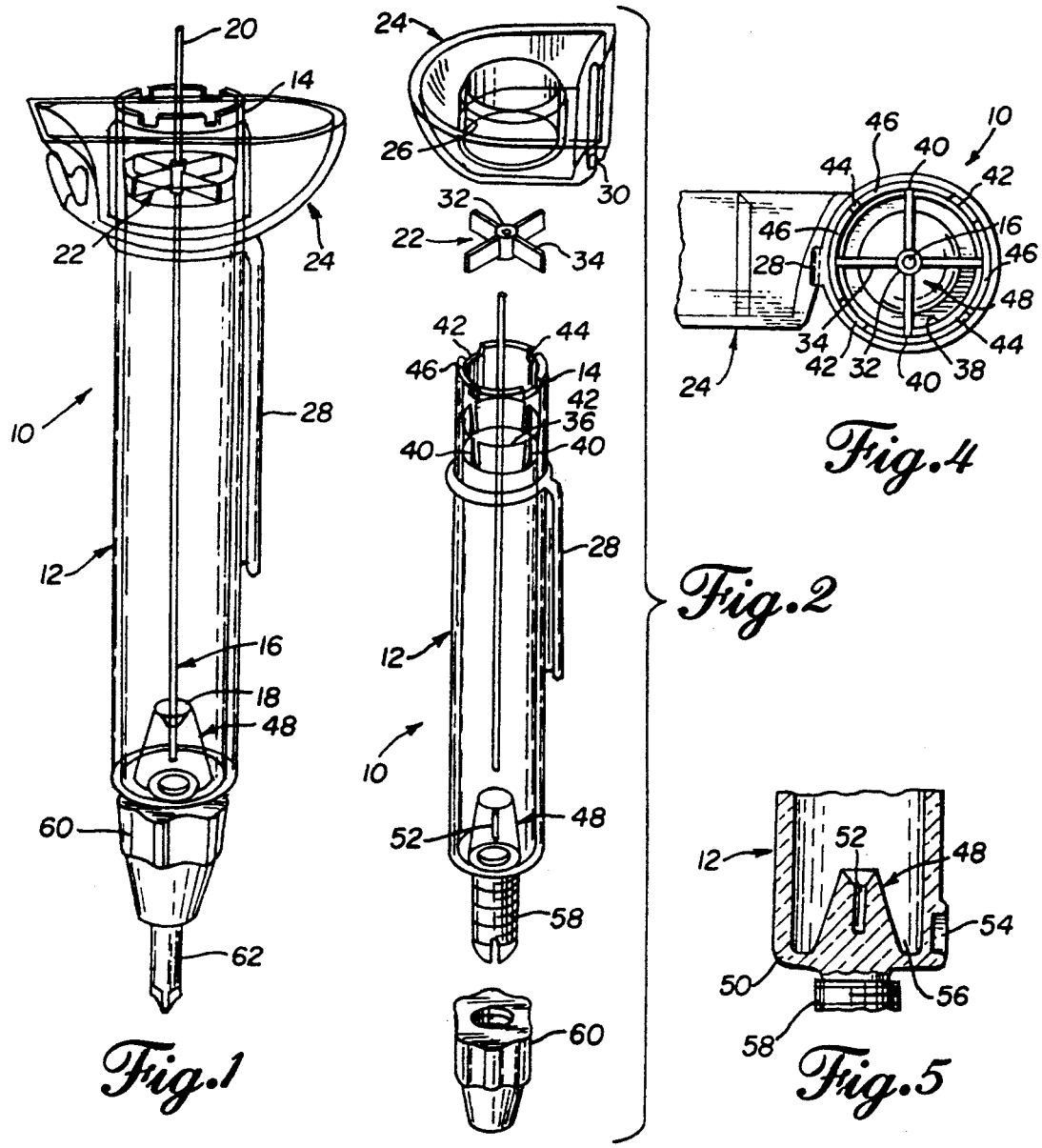

FUEL CHECKER FOR USE WITH PET COCK OR BALL AND SPRING DRAIN VALVES

BACKGROUND OF THE INVENTION

1. Field of the Invention

The present invention relates to hand tools, and more particularly to a tool designed for use in conjunction with fuel tank valves and incorporating a receptacle for receiving a specimen of the tank contents.

2. Description of the Related Art

As a recognized safety precaution, the nature of the fuel in aircraft gas tanks must be checked before each flight to determine the presence of any contaminating agents as well as the octane rating. In the past, this inspection has been effected by, for example, the opening of the tank quick drain valve, by any suitable means in allowing a portion of the fuel to flow outwardly for reception within any convenient type of container, such as a pan or the like. A scrutiny of the withdrawn fuel by an experienced individual will readily indicate whether the fuel is clear or is contaminated, and, further, as to what the octane rating of such fuel might be since its coloration is indicative thereof. In addition to withdrawing a specimen of the fuel from each tank of the aircraft, it is desired that a sample be taken from the lowermost location in the gas system, so that such procedure requires considerable time as well as effort in the requisite removal of any portions of the coweling to obtain access to the valve and operation of the valve itself.

Also, the like testing of fuels in the tank of gasoline powered ground vehicles, for example, in the military field, tanks, jeeps, half-tracks, and the like, is a desirable practice for assuming optimum operation. In the past this was accomplished by the use of any convenient instrumentalities, with all the associated inconvenience and time-consumption.

These tasks were made more convenient by the design of more specialized fuel checker devices. U.S. Pat. No. 3,011,349, issued to D. W. Kratz, entitled "Composite Tool and Receptacle", discloses a tool and receptacle for receiving specimens of aircraft gas tanks. The Kratz device utilizes an elongated body of circular cross-section with a closed lower end. The upper end edge is provided with a series of spaced apart, upwardly opening, generally U-shaped indentations or notches for engaging axially aligned actuating arms of a pet cock type quick drain valve. The elongated body is preferably formed of molded transparent plastic. The device has a screwdriver assembly integral to the bottom end of the elongated body which is handy during various operations typically involved with aircraft maintenance.

The Kratz device has been improved by other devices, the features of these devices being exemplified by a device disclosed in Sporty's Pilot Shop catalog, Oshkosh Issue, August thru November 1992, pg. 65. The Sporty's device is nearly identical to a device manufactured by ASA Company of Tacoma, Wash. The Sporty's/ASA device, like the Kratz device, utilizes a transparent elongated body of circular cross-section with a closed lower end and notches on the upper end for engaging a pet cock type valve. However, a plastic rod assembly is utilized for actuating a ball and spring type of drain valve.

The rod assembly includes a plurality of plastic, radially extending support leafs or extensions which extend from an intermediate portion of a plastic rod. The rod and support leafs are formed as a unitary integral assembly which is friction force fitted against the inner walls of the elongated body. The upper end of the rod extends beyond the open upper end of the elongated body to engage a ball and spring drain valve. The lower end of the rod remains unattached inside the elongated body. Although, to some degree, effective in its use with ball and spring type drain valves, the rod assembly of the Sporty's/ASA device is somewhat flimsy. The rod breaks off rather easily and the rod assembly is also vulnerable to being pushed down the elongated body during use due to the opposing force of the ball and spring valve.

As noted above, the Sporty's/ASA and the Kratz devices utilize a crenelated upper edge. In order to allow its use with varying sized pet cock drain valves, the Sporty's/ASA device utilizes different sized teeth, including small teeth. However, it has been found that the small teeth have been easily broken during use.

Another problem inherent with current fuel checking techniques involves inadvertant splashing of fuel. Typically, cups are used as splash guards. However, these cups cannot be stowed easily in the airplane.

OBJECTS AND SUMMARY OF THE INVENTION

It is therefore a principal object of the present invention to provide a tool compositively incorporating means for opening either a ball and spring type of drain valve or a pet cock type of drain and a receptacle for receiving a sample of a tank's contents.

Another object is to provide a more resilient means for supporting the rod used to actuate a ball and spring type of drain valve.

Another object is to provide a removable splash guard.

Another object is to provide a mechanism for preventing loss of the splash guard used in such a composite tool and to provide for its easy storage.

Still another object is to provide improved operation with pet cock type drain valves.

It is a still further object of the present to provide a composite tool for sampling tank contents which may be economically manufactured; which may be most easily utilized; and, which is durable and reliable in usage.

These and other objects are achieved by the present invention which is a hand-manipulative apparatus for receiving a specimen of the fuel tank contents of a fuel tank, the fuel tank being of the type utilizing either a pet cock drain valve or a ball and spring drain valve. In a broad aspect, the apparatus comprises an elongated body of substantially circular cross-section. The body is fabricated of transparent molded material and is open at its upper end. The body is of tubular character through a portion of its length for defining a fuel-receiving compartment having a central axis and communicating with the open upper end of the body. The body has a plurality of spaced-apart indentations in its upper end edge for alignment and cooperation with associated actuating arms of a pet cock drain valve, if such a pet cock drain valve is utilized. The tubular portion is closed at its lower end portion. A resilient semi-rigid rod is removably attached at a first end to the lower end portion of the tubular portion. The resilient rod extends along the central axis beyond the upper end edge of the body so as to engage and manipulate a ball and spring drain valve at a second end of the rod, if such a ball and spring drain valve is utilized. Additionally, the rod is supported at an intermediate portion thereof.

Supporting the rod at the first end (lower end) provides much more effective use with ball and spring type drain valves making it much less flimsy and incapable of being pushed down the elongated body during use by the opposing force of the ball and spring valve.

In another aspect, the invention includes an elongated guide formed on its exterior surface to cooperate with an elongated channel formed on an exterior of a splash guard. Thus, the splash guard can be conveniently stowed along the side of the elongated body when not in use and is therefore not easily lost. Other aspects of the present invention include a magnifying lens formed near the lower end portion of the elongated body and utilization of relatively long crenelations on the upper end edge surface of the elongated body.

The rod is preferably formed of a non-ferrous metal such as bronze.

Other objects, advantages, and novel features will become apparent from the following detailed description of the invention when considered in conjunction with accompanying drawings.

BRIEF DESCRIPTION OF THE DRAWINGS

FIG. 1 is a side perspective view of a composite apparatus constructed in accordance with and embodying the present invention, shown with the splash guard attached in an operative position.

FIG. 2 is an exploded perspective of the present invention.

FIG. 3 is a side view of the apparatus showing the splash guard in a stowed position.

FIG. 4 is a top plan view, with the splash guard in its stowed position.

FIG. 5 is an enlarged view, partially in cross-section, of the lower end of the elongated body, illustrating the centrally disposed forward extending member used to support the resilient rod at its lower end.

The same elements or parts throughout the figures of the drawings of the drawing are designated by the same reference characters.

DETAILED DESCRIPTION OF THE PREFERRED EMBODIMENTS

Referring to the drawings and the characters of reference marked thereon, FIG. 1 illustrates the apparatus of the invention in its operative, assembled position with a splash guard in place, the apparatus being designated generally as 10. The apparatus 10 includes an elongated body, designated generally as 12 which is preferably fabricated of transparent, molded plastic material such as plexiglas. Elongated body 12 is open at is upper end 14. It is primarily of tubular character, however, its lower end does include a screwdriver assembly, as will be described in more detail below.

Elongated body 12 defines a fuel receiving compartment having a central axis aligned with a resilient semi-rigid 16. Rod 16 is removably attached at a first (lower) end 18 to a lower end portion of the elongated body 12. The rod 16 extends along the central axis of the body 12 beyond the upper end edge so as to engage and manipulate a ball and spring drain valve at a second (upper) end 20 of the rod, if such a ball and spring drain valve is utilized. Means 22 are provided for supporting the rod 16 at an intermediate portion thereof. A splash guard 24 is slidably mounted on the upper end portion 14 of the elongated body 12 when in the operative position, as shown in FIG. 1.

Referring now to FIG. 2, some of the more particular aspects of this invention may be more easily seen. The upper end portion 14 of the elongated body has a slightly recessed outer surface. The splash guard 24 has an annular interior surface 26 thereon for cooperating with this recessed outer surface of the elongated body 12. Thus, a friction force fit is provided between these surfaces to allow the splash guard 24 to be slidably mounted on this upper end portion 14 of the elongated body 12.

The elongated body 12 further includes an axially disposed elongated guide 28 formed on its exterior surface. The splash guard 24 includes an elongated channel 30 formed on an exterior surface thereon. Therefore, the guide 28 and channel 30 cooperate to allow the splash guard 24 to be conveniently stowed along the side of the elongated body 12 when not in use. This stowed position is illustrated in FIGS. 3 and 4. In this stowed position the apparatus 10, including the splash guard 24, is relatively flat and can be stowed in a seat pocket or a side pocket of an airplane. (This is in contrast to the 'cups' that are currently typically used.)

Referring again to FIG. 2, means 22 for supporting rod 16 at an intermediate portion thereof comprises a resilient support member (or "spider") including an integral central hub 32 having an axially extending central opening defined therein and a plurality of radial extensions 34 projecting from the central hub 32. Support member 22 is preferably formed of plastic material. Rod 16 slides through the opening in the central hub 32, to the position shown in FIG. 1.

Line 36 defines a boundary line on the inner surface of the elongated body 12. Below this boundary line 36 the inner surface of elongated body 12 has a decreased diameter. This decreased diameter in the inner surface of elongated body 12 may be seen most clearly in FIG. 4, the decreased diameter inner surface being designated as 38. Decreased diameter portion 38 includes axially extending recesses 40 formed therein to cooperate with radial extensions 34 on support member 22 so as to secure the support member 22 in a friction force fit therein. The cooperation of extensions 34 with surface 38 may be seen clearly in FIG. 4.

As mentioned above, the body 12 includes a plurality of spaced-apart indentations and commensurate extensions at its upper end edge surface. As can be most clearly seen in FIG. 4, the spaced-apart indentations comprise two relatively long indentations 42 arranged 180 degrees from each other and two relatively short indentations 44 arranged 180 degrees from each other. The resulting axial extensions 46 are all relatively long. Thus, the invention may easily accommodate differently configured pet cock drain valves without sacrificing strength. The Kratz device and the Sporty's/ASA device, on the other hand, utilize relatively short extensions which break from time to time during use. Each of the extensions of the present invention forms an arc having an angle in the range of between about 65 degrees and 85 degrees, preferably about 75 degrees.

Referring now to FIG. 5, a centrally disposed forward extending member 48 is shown which is utilized to removably attach the first end 18 of the rod 16 to the lower end of the elongated body 12. Member 48 depends from the lower end portion 50 of the elongated body in a direction toward the upper end of that body 12. Member 48 is substantially conical and has a truncated apex with an opening 52 formed therein for providing a friction force fit when engaged with rod 16. Securement of the rod 16 at its lower end provides much greater support than the devices of the prior art.

It is noted that the present invention allows viewing of all of the fuel in the apparatus 10. Additionally, lower end portion 50 of elongated body 12 also preferably includes a magnifying lens 54 formed in the transparent molded material forming the elongated body 12. Conical forward extending member 48 forms a small volume 56 for fuel at the lowermost end 50 of the elongated body 12. Thus, member 48 cooperates synergistically with magnifying lens 54 to easily ascertain whether the fuel being tested is contaminated.

The present invention preferably includes a screwdriver assembly 58, 60, 62 which operates in a manner well known to those skilled in the art and is utilized to aid in typical maintenance operations including opening doors and removing cowling to gain access to certain drain cocks. The screwdriver assembly preferably utilizes a member 62 which is reversible, having a phillips blade on one end and a straight blade on the other end.

As can be seen in FIG. 5, the screwdriver subassembly 58 is positioned well below the floor of lower end 50 of the elongated body 12, thus when in the assembled state shown in FIG. 1 all of the contents of the body 12 are readily viewed. Prior art devices, such as the Sporty's/ASA device, have impeded views as a result of the presence of their correlative to adapter 60, which screws up slightly above the floor level, impeding the view of any contaminants which may come to rest on the floor.

The replaceable rod 16 is preferably formed of a non-ferrous, non-sparking metal, such as a bronze material. It may be, for example, approximately 3/32 inches in diameter. These rods are readily available in most hardware stores as bronze brazing rods and are therefore easily replaced.

Obviously, many modifications of the present invention are possible in light of the above teachings. It is therefore to be understood that, within the scope of appended claims, the invention may be practiced otherwise than as specifically described.

What is claimed and desired to be secured by Letters Patent of the United States is:

1. A hand-manipulative apparatus for receiving a specimen of the fuel tank contents of a fuel tank, said fuel tank of the type utilizing either a pet cock drain valve or a ball and spring drain valve, said apparatus comprising:
   a) an elongated body of substantially circular cross-section, said body being fabricated of transparent molded material and being open at its upper end, said body further being of tubular character through a portion of its length for defining a fuel-receiving compartment having a central axis and communicating with the open upper end of said body, said body having a plurality of spaced-apart indentations in its upper end edge, for alignment and cooperation with associated actuating arms of a pet cock drain valve, when such a pet cock drain valve is utilized, said tubular portion being closed at its lower end portion;
   b) a resilient, semi-rigid rod removably attached at a first end to said lower end portion of said tubular portion and extending along said central axis and beyond the upper end edge of said body so as to engage and manipulate a ball and spring drain valve at a second end of said rod, when such a ball and spring drain valve is utilized; and
   c) means for supporting said rod at an intermediate portion thereof.

2. The apparatus of claim 1 further including a centrally disposed forward extending member depending from said lower end portion of said tubular portion toward said upper end of said body, said forward extending member having an opening formed therein for provided a friction force fit with said rod.

3. The apparatus of claim 2 wherein said forward extending member is substantially conical, having a truncated apex, said opening being formed in said truncated apex.

4. The apparatus of claim 2 wherein a magnifying lens is formed in said transparent molded material of said elongated body, said magnifying lens being formed near the lower end portion of said tubular portion.

5. The apparatus of claim 2 further including a rearwardly extending screwdriver assembly depending from said lower end portion of said tubular portion.

6. The apparatus of claim 1 wherein said rod is formed of a non-ferrous metal.

7. The apparatus of claim 6 wherein said rod is formed of bronze material.

8. The apparatus of claim 1 wherein said rod is approximately 3/32 inches in diameter.

9. The apparatus of claim 1 further including a removable splash guard attachable near the upper end of said elongated body.

10. The apparatus of claim 9 wherein the upper end portion of said elongated body included a recessed outer surface, said splash guard having an annular interior surface thereon for cooperating with said recessed outer surface of said elongated body and providing a friction force fit therewith to allow said splash guard to be slidably mounted on said upper end portion of said elongated body.

11. The apparatus of claim 10 wherein said body further includes an axially disposed elongated guide formed on its exterior, and said splash guard includes an elongated channel formed on an exterior surface thereon, said guide and said channel cooperating to allow the splash guard to be conveniently stowed along the side of the elongated body when not in use.

12. The apparatus of claim 1 wherein means for supporting said rod at an intermediate portion thereof comprises a resilient support member including a central hub having an axially extending central opening defined therein and a plurality of radial extensions projecting from said central hub.

13. The apparatus of claim 12 wherein a portion of the inner surface of said elongated body includes axially extending recesses formed therein to cooperate with said radial extensions so as to secure said support member in a friction force fit therein.

14. The apparatus of claim 13 wherein said portion of said interior surface of said elongated body which includes said axially extending recesses has a decreased diameter.

15. The apparatus of claim 1 wherein said plurality of spaced-apart indentations in the upper end edge of said elongated body are alternately spaced with short and long indentations so as to accommodate variously sized actuating arms of said pet cock drain valves.

16. The apparatus of claim 15 wherein said spaced-apart indentations comprised two relatively long indentations arranged 180 degrees from each other and two relatively short indentations arranged 180 degrees from each other.

17. The apparatus of claim 5 wherein said screwdriver assembly is positioned sufficiently below said lower end portion of said tubular portion so as to allow an unimpeded viewing of all of the fuel contents in said elongated body.

* * * * *